US012590886B2

(12) United States Patent
Fujita et al.

(10) Patent No.: US 12,590,886 B2
(45) Date of Patent: Mar. 31, 2026

(54) OPTICAL MICROSCOPE AND IMAGING METHOD

(71) Applicants: Osaka University, Osaka (JP);
KYOTO PREFECTURAL PUBLIC UNIVERSITY CORPORATION, Kyoto (JP)

(72) Inventors: Katsumasa Fujita, Osaka (JP);
Kentaro Nishida, Osaka (JP); Hikaru Sato, Osaka (JP); Hideo Tanaka, Kyoto (JP); Yoshinori Harada, Kyoto (JP)

(73) Assignees: OSAKA UNIVERSITY, Osaka (JP);
KYOTO PREFECTURAL PUBLIC UNVERSITY CORPORATION, Kyoto (JP)

( * ) Notice: Subject to any disclaimer, the term of this patent is extended or adjusted under 35 U.S.C. 154(b) by 192 days.

(21) Appl. No.: 18/275,234

(22) PCT Filed: Jan. 19, 2022

(86) PCT No.: PCT/JP2022/001688
§ 371 (c)(1),
(2) Date: Aug. 1, 2023

(87) PCT Pub. No.: WO2022/163445
PCT Pub. Date: Aug. 4, 2022

(65) Prior Publication Data
US 2024/0102924 A1     Mar. 28, 2024

(30) Foreign Application Priority Data

Feb. 1, 2021     (JP) ................................. 2021-014272

(51) Int. Cl.
*G01N 21/31* (2006.01)
*G01N 33/483* (2006.01)
*G02B 21/00* (2006.01)

(52) U.S. Cl.
CPC ......... *G01N 21/31* (2013.01); *G01N 33/4833* (2013.01); *G02B 21/0032* (2013.01); *G01N 2201/06113* (2013.01)

(58) Field of Classification Search
CPC .... G01N 21/63; G01N 21/64; G01N 21/6458; G02B 21/0076
See application file for complete search history.

(56) References Cited

U.S. PATENT DOCUMENTS 9,001,321 B2 *   4/2015   Fujita ................... G02B 21/002
                                                            356/301
2008/0215272 A1     9/2008   Fujita et al.
(Continued)

FOREIGN PATENT DOCUMENTS

JP        2015-197606 A     11/2015
JP        2020-523615 A     8/2020
(Continued)

OTHER PUBLICATIONS

Tian, Peifang et al.; "Ultrafast measurement of two-photon absorption by loss modulation"; Optics Letters; vol. 27, No. 18; Sep. 15, 2002; 3 pages.
(Continued)

*Primary Examiner* — Kara E. Geisel
(74) *Attorney, Agent, or Firm* — Lippes Mathias LLP

(57)     ABSTRACT

A diagnostic optical microscope according to the present embodiment includes at least one laser light source (11) configured to generate laser light for illuminating a sample (40) containing a light absorbing material, a lens configured to focus the laser light to be focused on the sample (40), scanning means for changing a focusing position of the laser light on the sample (40), and a light detector (31) configured to detect laser light transmitted through the sample (40) as signal light. A laser light intensity is changed to obtain a nonlinear region in which the laser light intensity and a
(Continued)

signal light intensity have a nonlinear relation due to occurrence of saturation of absorption in the light absorbing material when the laser light intensity is maximized. An image is generated based on a nonlinear component of the signal light based on the saturation of absorption in the light absorbing material.

10 Claims, 17 Drawing Sheets

(56)  References Cited

U.S. PATENT DOCUMENTS

| | | | | |
|---|---|---|---|---|
| 2012/0112098 A1* | 5/2012 | Hoyt | .......................... | G06T 5/50 |
| | | | | 250/459.1 |
| 2012/0307238 A1 | 12/2012 | Fujita et al. | | |
| 2017/0082546 A1 | 3/2017 | Dake et al. | | |
| 2020/0192072 A1 | 6/2020 | Husher et al. | | |
| 2020/0327657 A1* | 10/2020 | Klaiman | ............... | G06T 7/0012 |

FOREIGN PATENT DOCUMENTS

| | | | |
|---|---|---|---|
| WO | 2006061947 A1 | 6/2006 | |
| WO | 2011099269 A1 | 8/2011 | |

OTHER PUBLICATIONS

Sasaki, Keiji et al.; "Condocal laser-induced absorption microscope"; J. Opt. Soc. Am A; vol. 9, No. 6; Jun. 1992; 5 pages.
International Search Report of PCT/JP2022/001688, dated Mar. 28, 2022, 4 pages.

* cited by examiner

CHANGE IN INTENSITY WITH TIME

AMPLITUDE SPECTRUM

CHANGE IN INTENSITY WITH TIME

Time

AMPLITUDE SPECTRUM

Frequency

LINEAR SIGNAL (f)          NONLINEAR SIGNAL (2f)

PROFILE

LINEAR SIGNAL (f)                    NONLINEAR SIGNAL (2f)

Signal [a.u.]

PROFILE

OPTICAL MICROSCOPE AND IMAGING METHOD

TECHNICAL FIELD

The present invention relates to an optical microscope and a method for imaging an image, and more particularly relates to a technology for acquiring an image to be used for tissue observation or pathological diagnosis.

BACKGROUND ART

Non Patent Literature 1 and Non Patent Literature 2 disclose high-resolution transmission optical microscopes. Non Patent Literature 1 utilizes two photon absorption, and Non Patent Literature 2 utilizes transient absorption. In Patent Literature 1, the laser light intensity is changed such that a nonlinear region is obtained in which the laser light intensity and the signal light intensity have a nonlinear relation due to occurrence of saturation or nonlinear increase of signal light. Observation is performed based on a saturation component or a nonlinear increase component of the signal light.

Patent Literature 2 discloses a fluorescence microscope that detects fluorescence from a sample. In Patent Literature 2, the laser light intensity is changed such that saturation of fluorescence occurs when the laser light intensity is maximized. Observation is performed based on a saturation component of fluorescence.

CITATION LIST

Patent Literature

[Patent Literature 1] International Patent Publication No. WO 2011/99269
[Patent Literature 2] International Patent Publication No. WO 2006/061947

Non Patent Literature

[Non Patent Literature 1] Tian, et al., Opt. Lett., 27, 1634-1636 (2002)
[Non Patent Literature 2] Sasaki, et al., J. Opt. Soc. Am. A, 9, 932-936 (1992)

SUMMARY OF INVENTION

It is requested that optical microscopes for imaging an image to be used for pathological diagnosis, tissue observation, or the like should have a simpler configuration. For example, an inexpensive optical microscope having a simple configuration can be more widespread.

Non Patent Literature 1 and Non Patent Literature 2 are difficult to achieve simplified apparatus configurations due to the use of two photon absorption or transient absorption. For example, excitation with pulse laser is required to induce a nonlinear optical effect. Pulse laser is expensive and difficult to handle, and therefore difficult to utilize for pathological diagnosis or tissue observation.

In Claim 5 of Patent Literature 1, optical harmonics due to a higher-order nonlinear optical effect is generated. The need to generate optical harmonics makes it difficult to achieve a simpler apparatus configuration. In Patent Literature 2, fluorescence is detected with a light detector. Thus, it is requested that a higher S/N ratio should be achieved.

An optical microscope according to the present embodiment is an optical microscope for imaging an image for tissue observation or pathological diagnosis, including at least one laser light source configured to generate laser light for illuminating a sample containing a light absorbing material, a lens configured to focus the laser light to be focused on the sample, scanning means for changing a focusing position of the laser light on the sample, and a light detector configured to detect laser light transmitted through the sample as signal light. A laser light intensity is changed to obtain a nonlinear region in which the laser light intensity and a signal light intensity have a nonlinear relation due to occurrence of saturation of absorption in the light absorbing material when the laser light intensity is maximized. An image is generated based on a nonlinear component of the signal light based on the saturation of absorption in the light absorbing material.

In the above-described optical microscope, the light absorbing material may be a dye, and the sample may contain a tissue, a cell, or a bacterium stained with the dye.

In the above-described optical microscope, the dye that stains the sample may be Eosin Y, and a product CL of a concentration C of the dye and a thickness L of the sample may be $4.0 \times 10^{-9}$ mol/cm$^2$ or smaller.

In the above-described optical microscope, in a case where the laser light is intensity-modulate with a modulation frequency f, and a product of a concentration C of the dye and a thickness L of the sample is denoted by a product CL, a value of the product CL may be included in a range in which an inclination of a modulation harmonic component of the modulation frequency f included in a transmission signal is positive with respect to the product CL.

In the above-described optical microscope, the focusing position of the laser light may be changed in a thickness direction of the sample.

In the above-described optical microscope, the laser light source may generate CW (continuous wave) laser light. This can achieve a simplified apparatus configuration.

In the above-described optical microscope, the laser light incident on the sample may be pulse laser light.

An imaging method according to the present embodiment is an imaging method for imaging an image for tissue observation or pathological diagnosis using an optical microscope, the imaging method including the steps of generating laser light for illuminating a sample containing a light absorbing material, focusing the laser light to be focused on the sample, changing a focusing position of the laser light on the sample, detecting laser light transmitted through the sample as signal light, changing a laser light intensity to obtain a nonlinear region in which the laser light intensity and a signal light intensity have a nonlinear relation due to occurrence of saturation of absorption in the light absorbing material when the laser light intensity is maximized, and generating an image based on a nonlinear component of the signal light based on the saturation of absorption in the light absorbing material.

In the above-described imaging method, the light absorbing material may be a dye, and the sample may contain a tissue, a cell, or a bacterium stained with the dye.

In the above-described imaging method, the dye that stains the sample may be Eosin Y, and a product CL of a concentration C of the dye and a thickness L of the sample may be $4.0 \times 10^{-9}$ mol/cm$^2$ or smaller.

In the above-described imaging method, in a case where the laser light is intensity-modulated with a modulation frequency f, and a product of a concentration C of the dye and a thickness L of the sample is denoted by a product CL, a value of the product CL may be included in a range in which an inclination of a modulation harmonic component of the modulation frequency f included in a transmission signal is positive with respect to the product CL.

In the above-described imaging method, the focusing position of the laser light may be changed in a thickness direction of the tissue sample.

In the above-described imaging method, the laser light may be CW (continuous wave) laser light. This can achieve a simplified apparatus configuration.

In the above-described imaging method, the laser light incident on the sample may be pulse laser light.

According to the present invention, it is possible to provide a diagnostic optical microscope that can image a diagnostic image simply with a high resolution, and a method for imaging a diagnostic image.

DESCRIPTION OF EMBODIMENTS

Figure 1:
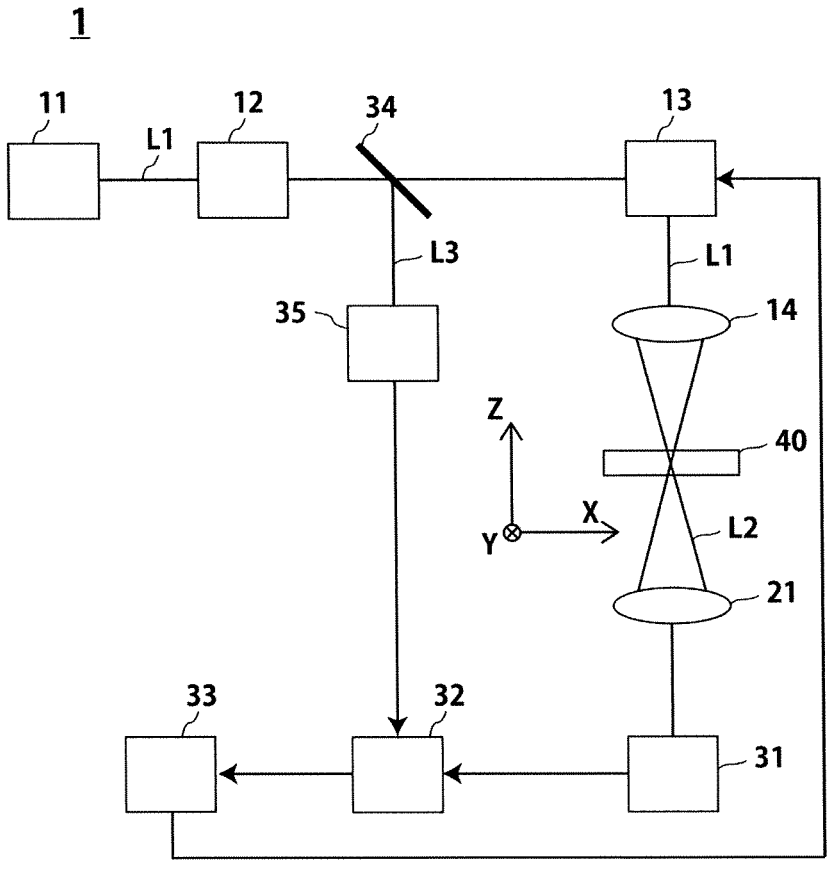
FIG. 1 is a diagram showing a configuration of a diagnostic optical microscope according to a first embodiment.

Hereinafter, an embodiment to which the present invention can be applied will be described. The following description is to describe the embodiment of the present invention, and the present invention is not limited to the following embodiment. Omission and simplification are made in the following description as appropriate for clear description. Those skilled in the art would easily modify, add, or exchange each element in the following embodiment within the scope of the present invention. The same elements are denoted by an identical reference numeral in the respective drawings, and description is omitted as appropriate.

An optical microscope according to the present embodiment images a sample for pathological diagnosis to acquire a diagnostic image. Specifically, a tissue sample is stained with a dye such as Eosin Y. By imaging the tissue sample with the optical microscope, a diagnostic image can be acquired. For example, the following diseases and tissues are targeted for pathological diagnoses.

Kidney tissues (biopsy for various inflammations such as glomerulonephritis)

Functional tumors of endocrine organs except goiter (such as pituitary adenoma, adrenocortical adenoma, and islet adenoma)

Ectopic hormone-producing tumors (such as carcinoid)

Soft-tissue sarcomas (such as liposarcoma, leiomyosarcoma, rhabdomyosarcoma, and neurofibroma)

Lipid storage diseases (such as Gaucher's disease and Niemann-Pick disease)

Polysaccharide storage diseases

Myocardial biopsy (myocardiopathy)

As a matter of course, a tissue sample imaged with the optical microscope in the present embodiment, a disease diagnosed from a diagnostic image of the tissue sample, and the like are not limited to the above-described examples. The optical microscope of the present embodiment images a diagnostic image of a tissue sample stained with a dye. Specifically, the optical microscope of the present embodiment performs detection with a high spatial resolution utilizing saturation of absorption in the dye. An image for tissue observation or pathological diagnosis can be imaged with a high resolution.

The sample can be a cell, a tissue, a bacterium, or the like stained with a dye. Note that the sample may not be stained with the dye. That is, the sample should only contain a light absorbing material. For example, the light absorbing material should only be a material which absorbs laser light and in which saturation of absorption occurs when the laser light intensity is increased.

First Embodiment

A diagnostic optical microscope and an imaging method therewith according to a first embodiment will be described using FIG. 1. FIG. 1 is a diagram showing an optical microscope 1. The optical microscope 1 includes a laser light source 11, a modulator 12, a galvano-mirror 13, and an objective lens 14. The optical microscope 1 further includes a condenser lens 21, a light detector 31, a lock-in amplifier 32, a processing unit 33, a beam sampler 34, and a reference light detector 35.

First, an illumination optical system for illuminating a sample 40 will be described. The laser light source 11 generates laser light L1 for illuminating the sample 40. The laser light source 11 is a continuously oscillating CW (continuous wave) laser light source. The laser light source 11 is excitation light that excites a dye in the sample 40. For example, the laser light L1 has a central wavelength λ of 532 nm. The laser light L1 from the laser light source 11 is incident on the modulator 12.

Figure 2:
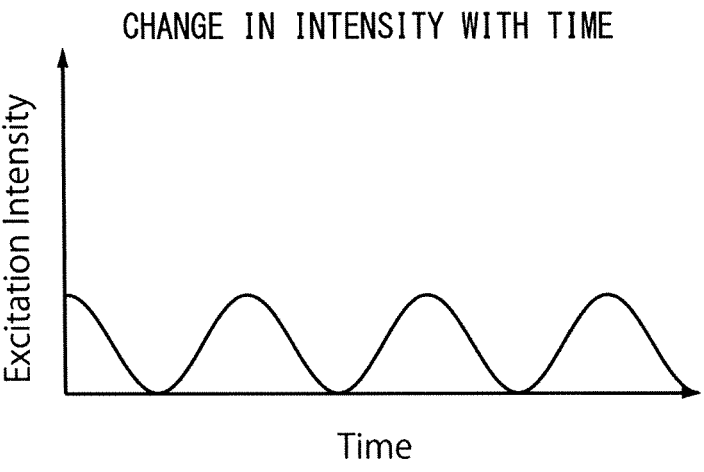
FIG. 2 is a graph showing a change with time in laser light intensity after modulation.

The modulator 12 is an AOM (acousto-optic modulator), for example. The modulator 12 modulates the laser light intensity of the laser light L1. That is, the laser light intensity (hereinafter also briefly referred to as the intensity) changes according to time. Herein, the intensity is modulated such that the laser light intensity (excitation light intensity) temporally changes with a single frequency as shown in FIG. 2. Note that FIG. 2 is a graph showing the laser light intensity after modulation, the horizontal axis representing time, and the vertical axis representing laser light intensity.

The intensity of the laser light L1 is temporally modulated by the modulator 12 with a modulation frequency f. The modulation frequency f is 10 kHz, for example. As a matter of course, the modulation frequency f is not limited to a particular value. The modulator 12 is not limited to the AOM, but an electro-optic modulator (EOM) may be used.

The laser light L1 from the modulator 12 passes through the beam sampler 34. The beam sampler 34 is a transparent glass substrate or the like, and reflects and takes out part of the laser light L1. The laser light L1 taken out by the beam sampler 34 is referred to as reference light L3. The reference light L3 reflected by the beam sampler 34 is detected by the reference light detector 35. The reference light detector 35 outputs a reference light signal in accordance with the amount of light of the reference light L3 to the lock-in amplifier 32.

The laser light L1 passed through the beam sampler 34 is incident on the galvano-mirror 13. The galvano-mirror 13 is scanning means for scanning the sample 40 with a focusing position of the laser light L1. The galvano-mirror 13 deflects the laser light L1 to scan the sample 40. Herein, the galvano-mirror 13 is an optical scanner that scans the sample 40 with the laser light L1 in the X-direction and the Y-direction. Thus, the sample 40 is scanned two-dimensionally with an illuminated position of the laser light L1. Note that the X-direction and the Y-direction are directions orthogonal to an optical axis of the objective lens 14 and orthogonal to each other.

The laser light L1 reflected by the galvano-mirror 13 is incident on the objective lens 14. The objective lens 14 focuses the laser light L1 on the sample 40. A numeric aperture and a magnification of the objective lens 14 are not limited to particular values.

The objective lens 14 focuses the laser light L1 on the sample 40. The laser light L1 focused by the objective lens 14 illuminates the sample 40. In addition, a relative illuminated position on the sample 40 is changed by the galvano-mirror 13. In addition, the scanning means for scanning the sample 40 with the illuminated position is not limited to the galvano-mirror 13. For example, a drive stage on which the sample 40 is arranged, or the like may be used as the scanning means. As a matter of course, they may be combined together. For example, the sample 40 may be scanned in the X-direction with the galvano-mirror 13, and may be scanned in the Y-direction with the stage.

The scanning means should only be configured to scan the sample 40 while changing relative positions of the laser light L1 and the sample 40. Note that the scanning is not only limited to two-dimensional scanning, but may be performed three-dimensionally. For example, the sample 40 may be scanned in the Z-direction by changing the distance between the sample 40 and the objective lens 14. This enables a three-dimensional image or a tomographic image to be imaged.

The sample 40 is a tissue sample for pathological diagnosis. That is, the sample 40 is a tissue sample harvested from a patient. The sample 40 is stained with a dye. The wavelength of the laser light L1 is an excitation wavelength of the dye. The laser light L1 is absorbed into the dye in the sample 40. Part of the laser light L1 becomes transmitted light transmitted through the sample 40.

Next, a detection optical system for detecting signal light from the sample 40 will be described. The laser light L1 transmitted through the sample 40 is referred to as signal light L2. The signal light L2 is focused by the condenser lens 21. It is preferable to use the condenser lens 21 having a numeric aperture identical to or higher than the numeric aperture of the objective lens 14. Note that it is also possible to omit the condenser lens 21.

The signal light L2 is incident on the light detector 31. The light detector 31 detects the signal light L2 focused by the condenser lens 21. The light detector 31 is a photomultiplier tube (PMT) or a photodiode (PD), for example. The light detector 31 outputs a detection signal in accordance with the amount of detected light of the signal light L2 to the lock-in amplifier 32.

The lock-in amplifier 32 locks in a predetermined repetition frequency, and lock-in detects a signal from the light detector 31. Here, the lock-in amplifier 32 receives a reference light signal from the reference light detector 35. The reference light signal is intensity-modulated with the modulation frequency f. The lock-in amplifier 32 demodulates the signal with a frequency n times (n is an integer of 2 or more) as high as the modulation frequency f. For example, in a case of assuming that the modulation frequency f is 10 kHz, demodulation is performed with a frequency of 20 kHz, 30 kHz, . . . . This enables a nonlinear component of the signal light L2 to be extracted and detected.

The processing unit 33 is an information processing apparatus such as a personal computer, and stores a detection signal from the lock-in amplifier 32. The processing unit 33 controls the galvano-mirror 13 to scan the sample 40 with excitation light. The processing unit 33 associates the detection signal with a scanning position of the galvano-mirror 13. Further, the processing unit 33 forms an optical image based on the signal output from the lock-in amplifier 32.

When a predetermined operation is performed in the processing unit 33, the optical image can be displayed on a screen. The processing unit 33 can also store data on the optical image in a memory or the like. This enables the sample 40 to be observed and imaged with transmitted light transmitted through the sample 40. Further, the processing unit 33 generates a diagnostic image based on the nonlinear component of the signal light L2 based on saturation of absorption in the dye. Generation of the diagnostic image will be described later.

Figure 3:
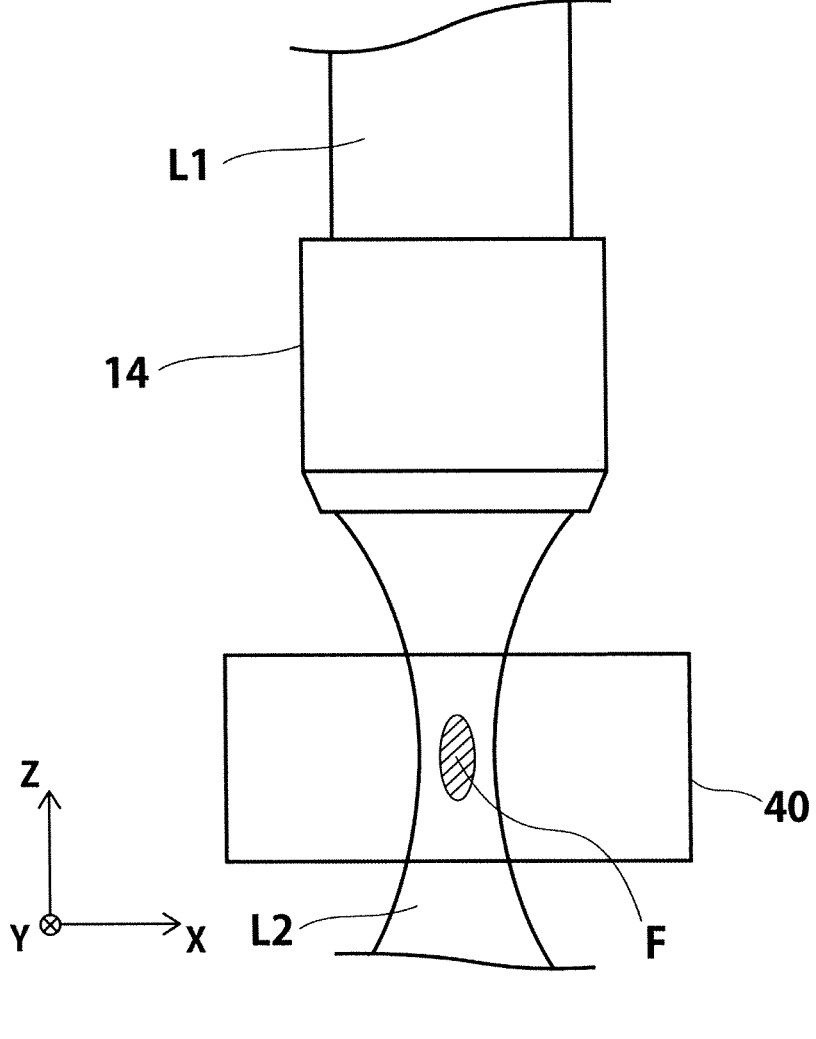
FIG. 3 is a schematic diagram showing a sample illuminated with laser light.
Figure 4:
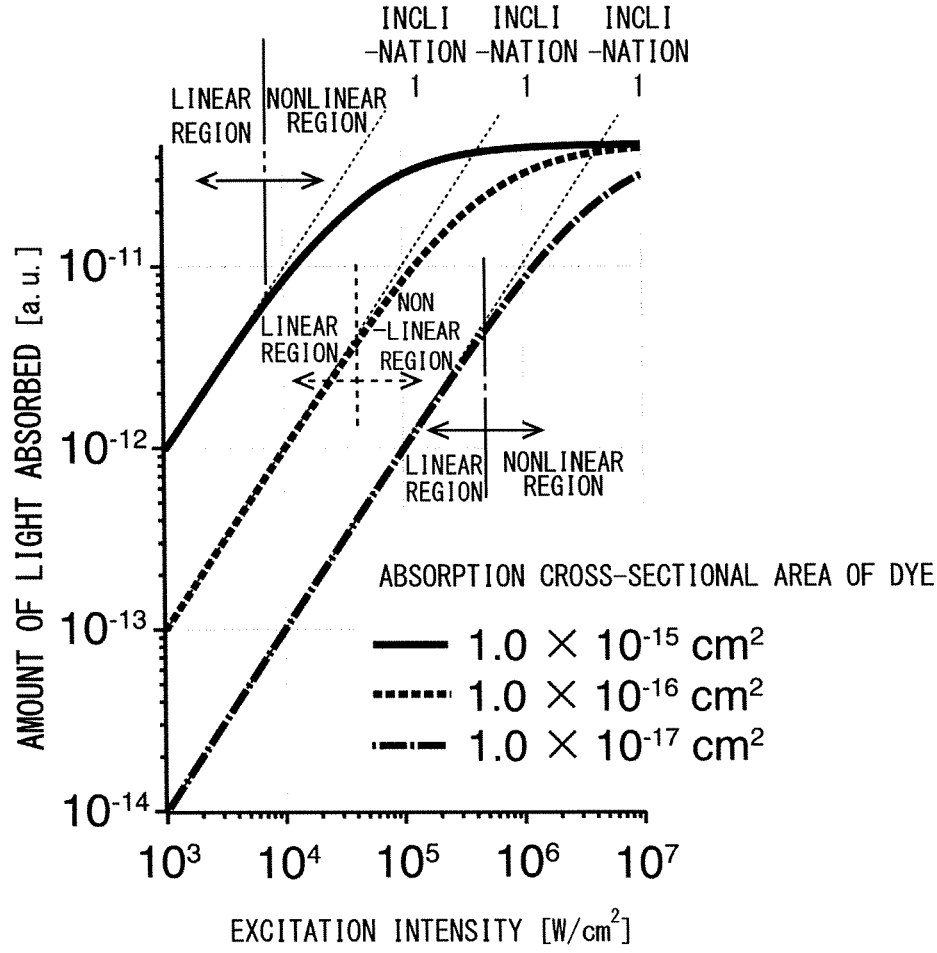
FIG. 4 is a graph showing a relation between excitation light intensity and amount of light absorbed by a dye.

The modulator 12 changes the laser light intensity to obtain a nonlinear region in which the laser light intensity and a signal light intensity have a nonlinear relation due to occurrence of saturation of absorption in the dye when the laser light intensity is maximized. This point will be described using FIG. 3 and FIG. 4. FIG. 3 is a schematic diagram showing a focal point of the objective lens 14 and its vicinity. FIG. 4 is a graph showing a relation between the excitation light intensity and absorption power in the dye. In FIG. 4, the horizontal axis represents excitation light intensity (laser light intensity), and the vertical axis represents the amount of light absorbed by the dye.

As shown in FIG. 3, the objective lens 14 focuses the laser light L1 on the sample 40. Consequently, a focal point F of the laser light L1 is formed in the sample 40. For example, a spatial distribution of the intensity of the laser light L1 on an XY-plane is a Gaussian distribution. The laser light intensity (excitation light intensity) is the highest at the center of the focal point F. Further, the laser light intensity decreases with distance from the focal point F.

In a case of detecting transmitted light with a common laser scanning microscope, absorption of laser light generates contrast in an image. Consequently, the resolution of the common laser transmission microscope is restricted by a spot size of laser light focused by an objective lens. That is, the resolution is restricted by the laser light wavelength and the numeric aperture of the objective lens. In addition, the laser light is absorbed by the entire sample 40 in the Z-direction. Thus, in a case where the thickness of the sample 40 in the Z-direction is large, the laser light will also be absorbed at places other than a focal plane. Thus, it is difficult to image a high-resolution diagnostic image with the common laser transmission microscope. It is also difficult to image a high-resolution diagnostic image with a wide-field transmission microscope (a bright field microscope) to be used for a pathological diagnosis due to light absorption in front of and behind an observation plane.

Thus, the present embodiment utilizes absorption saturation in the dye. The laser light L1 becomes excitation light that excites the dye. As the excitation light intensity is raised, the amount of light absorbed into the dye increases. As shown in FIG. 4, as the excitation light intensity rises, the amount of light absorbed by the dye increases. In the linear region, the excitation light intensity and the amount of light absorbed have a linear relation (proportional relation) as shown in FIG. 4. Further, when the excitation light intensity rises to some degree, saturation of absorption occurs in the dye. When saturation of absorption in the dye occurs, the relation between the excitation light intensity and the amount of light absorbed becomes nonlinear.

Here, a region in which a relation between the excitation light intensity and the amount of light absorbed is nonlinear is referred to as a nonlinear region. The nonlinear region is a region in which the excitation light intensity is higher than in the linear region. In the linear region, the relation between the excitation light intensity and the amount of light absorbed matches a straight line having an inclination of 1, while in the nonlinear region, the relation departs from the straight line having the inclination of 1, and the inclination becomes less than 1. Further, as the excitation light intensity rises, the inclination decreases. Note that the boundary between the nonlinear region and the linear region differs in accordance with the absorption cross-sectional area of the dye.

Figure 5:
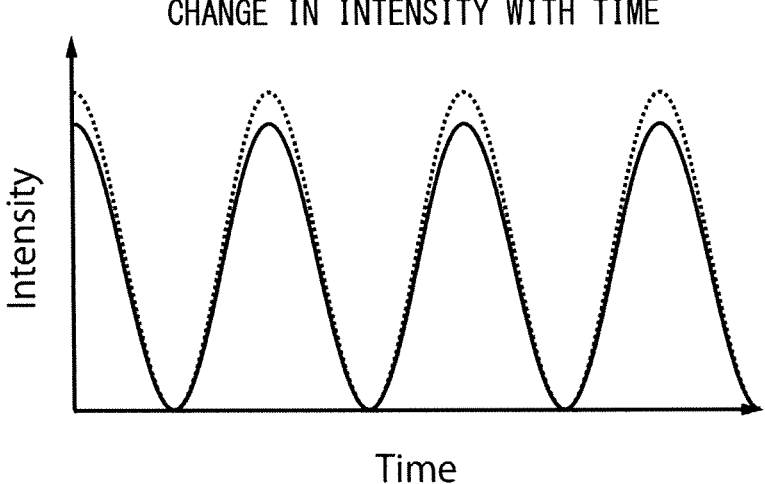
FIG. 5 includes graphs for describing a relation between excitation light intensity and intensity of transmitted light from the dye at a focal point.
Figure 5:
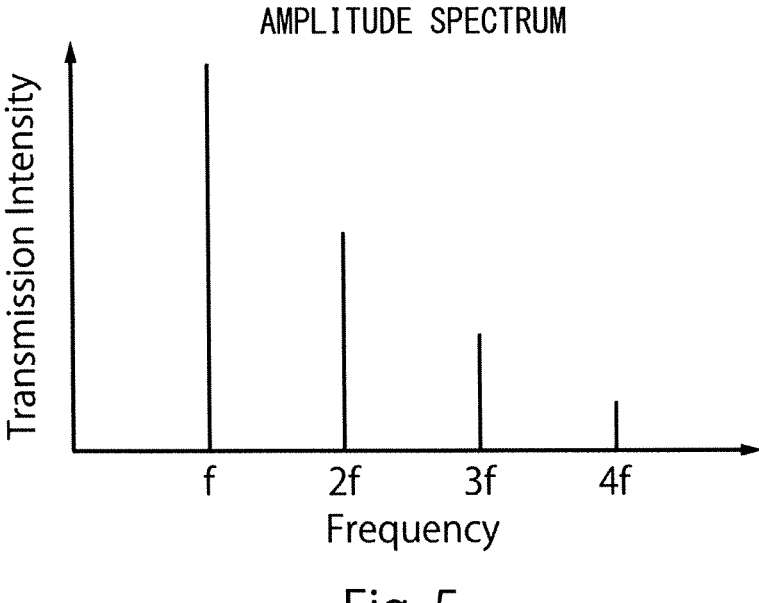
Figure 6:
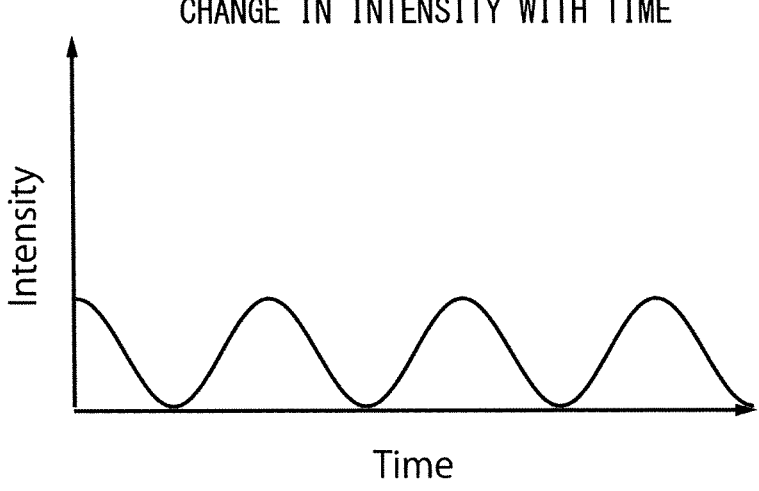
FIG. 6 includes graphs for describing a relation between excitation light intensity and intensity of transmitted light from the dye at a non-focal point.
Figure 6:
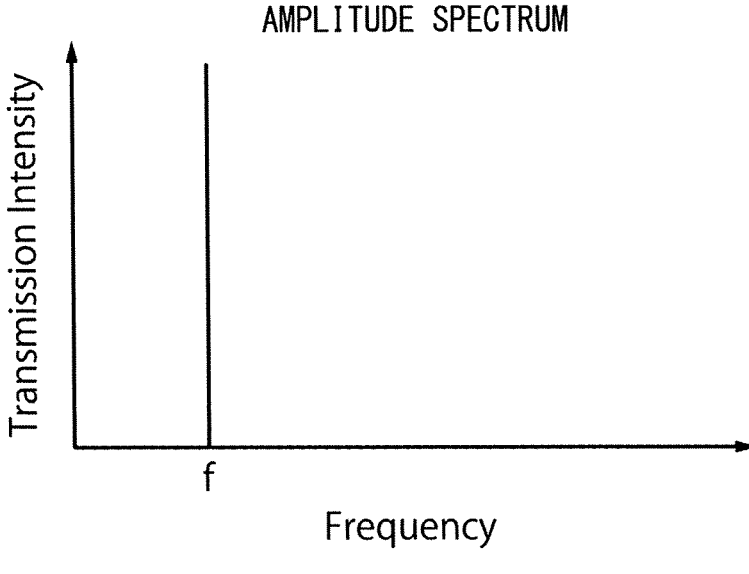

FIG. 5 includes diagrams showing the excitation light intensity and the transmitted light intensity at the focal point F, and FIG. 6 includes diagrams showing the excitation light intensity and the transmitted light intensity at a non-focal point. Upper graphs in FIG. 5 and FIG. 6 show graphs showing respective changes with time in excitation light intensity and transmitted light intensity, the horizontal axis representing time t, and the vertical axis representing excitation light intensity and transmitted light intensity. Lower graphs in FIG. 5 and FIG. 6 show amplitude spectrums obtained by Fourier-transforming the transmitted light intensity.

In addition, in the graphs showing the changes with time, the solid line represents the excitation light intensity, and the broken line represents the transmitted light intensity. Illustration in FIG. 5 and FIG. 6 is made assuming that waveforms of the excitation light intensity and the transmitted light intensity match each other in a state where absorption in the dye is not saturated. Consequently, at the non-focal point, the graphs of the excitation light intensity and the transmitted light intensity overlap each other.

At the focal point F, saturation of absorption in the dye occurs because the excitation light intensity is high. Consequently, a nonlinear increase in accordance with saturation of absorption occurs in transmitted light transmitted through the dye. As shown in FIG. 5, absorption power is saturated and a nonlinear increase occurs in the transmitted light at the timing when the excitation light intensity reaches a peak and in the vicinity of the timing. Note that the absorption power is not saturated at the timing when the excitation light intensity reaches bottom at the focal point F, so that a nonlinear increase in transmitted light does not occur. An amplitude spectrum obtained by Fourier-transforming the transmitted light intensity at the focal point F is a line spectrum having peaks at frequencies (f, 2f, 3f, 4f, . . . ) which are integral multiples of the modulation frequency f.

On the other hand, the excitation light intensity is low at the non-focal point, so that saturation of absorption in the dye does not occur even at the timing when the excitation light intensity reaches a peak. That is, saturation of absorption in the dye does not occur at any timing at the non-focal point, causing the excitation light intensity and the transmitted light intensity to have a linear relation. The amplitude spectrum obtained by Fourier-transforming the transmitted light intensity at the non-focal point is a line spectrum having a peak only with the modulation frequency f.

In this manner, absorption in the dye is saturated at the focal point F. An absorption saturation component decreases with distance from the focal point F. A nonlinear increase component of the transmitted light in accordance with saturation of absorption decreases with distance from the focal point F. In other words, the nonlinear increase component of the transmitted light in accordance with saturation of absorption increases toward the center of the focal point F.

In this manner, when the excitation light intensity is low, the excitation light intensity and the transmitted light intensity are proportional, but when the excitation light intensity rises up to the nonlinear region, the excitation light intensity and the transmitted light intensity are no longer proportional. The light detector 31 detects transmitted light transmitted through the sample 40 as the signal light L2. When the laser light intensity is raised, the nonlinear increase component occurs in the signal light L2 detected by the light detector 31. The nonlinear increase component of signal light is more likely to occur as the laser light intensity increases. Further, as the laser light intensity increases, the nonlinear increase component included in the signal light increases. The processing unit 33 generates a diagnostic image in accordance with the nonlinear component of the signal light L2.

Figure 7:
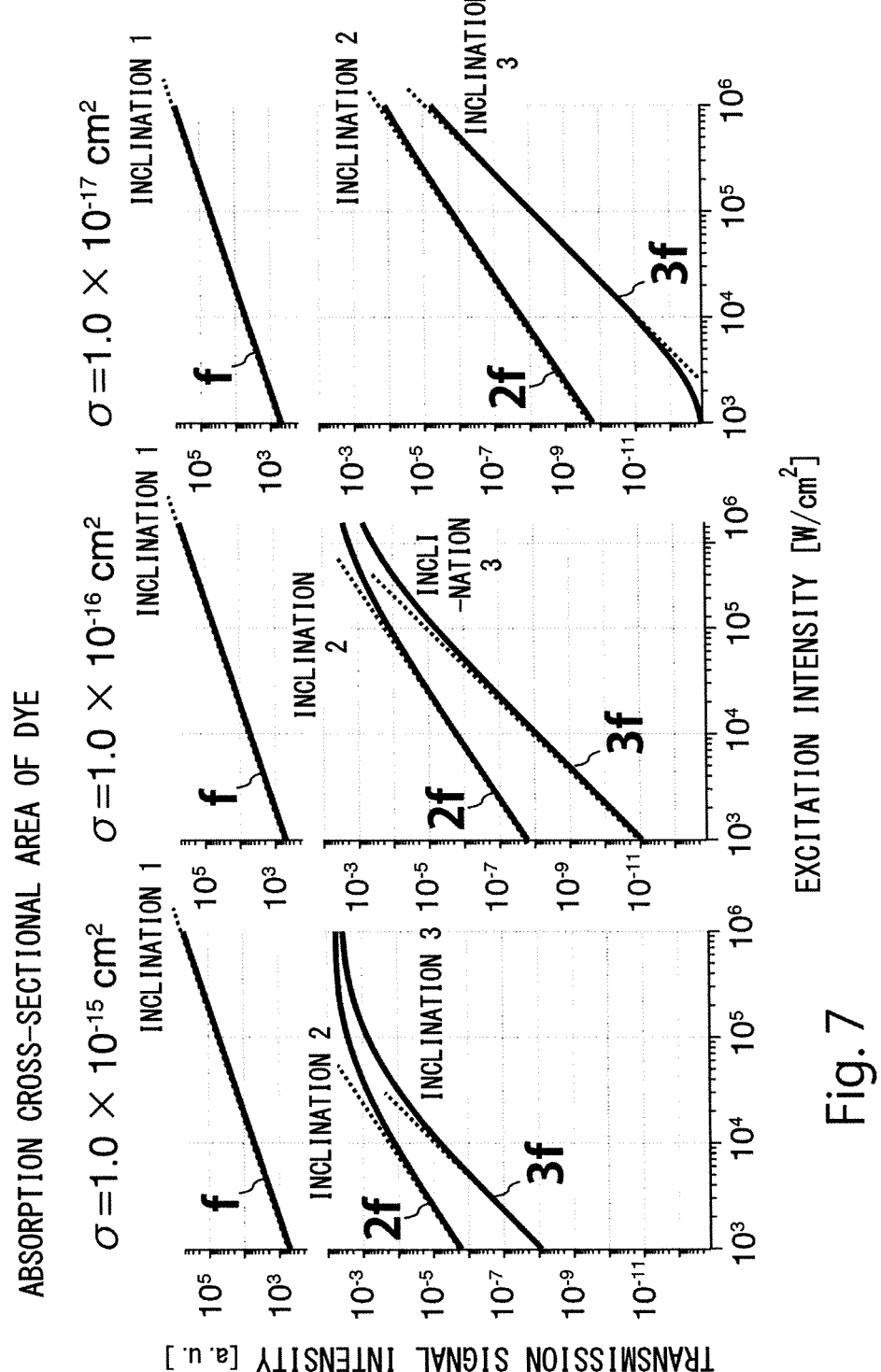
FIG. 7 includes graphs showing relations of excitation light intensity to a modulation frequency component of transmitted light intensity and its harmonic components.

FIG. 7 includes graphs showing calculation results of the relation between the excitation light intensity and the signal light intensity. The horizontal axis represents excitation the signal light intensity, and the vertical axis represents signal intensity. The signal light intensities in FIG. 7 respectively show the modulation frequency component (f), a modulation harmonic component (2f) twice as high as the modulation frequency f, and a modulation harmonic component (3f) three times as high as the modulation frequency f.

Optical physical property values of Eosin Y molecules are used for the calculations in FIG. 7. The modulation frequency f of the excitation light is 10 kHz, and is assumed to have a wavelength of 532 nm.

A relation between the transmission signal demodulated with the modulation frequency component (f) and the excitation intensity matches the inclination of 1. That is, the transmission signal demodulated with the modulation frequency component (f) is a linear signal. On the other hand, transmission signals demodulated with the modulation harmonics (2f) twice as high as the modulation frequency f and the modulation harmonics (3f) three times as high as the modulation frequency f respectively show second-order and third-order nonlinear increases with respect to the excitation intensity. That is, demodulation of the transmission signal with the modulation harmonics (2f) twice as high as the modulation frequency f and the modulation harmonics (3f) three times as high as the modulation frequency f enables second-order and third-order nonlinear signal components of the transmission signal to be detected respectively.

Figure 8:
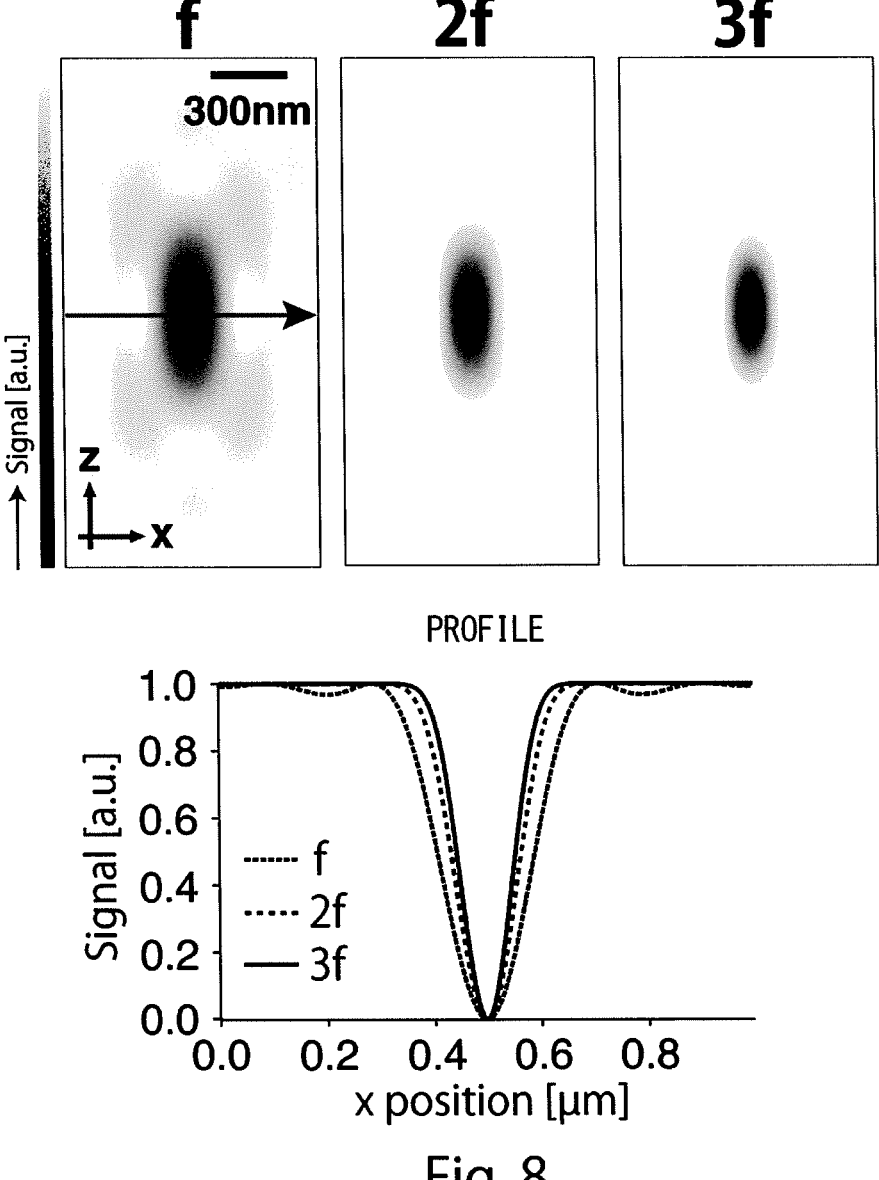
FIG. 8 includes diagrams showing images of minute point composed of the modulation frequency component of a transmitted light signal and its harmonic components as well as profiles of the images in an x-direction.
Figure 9:
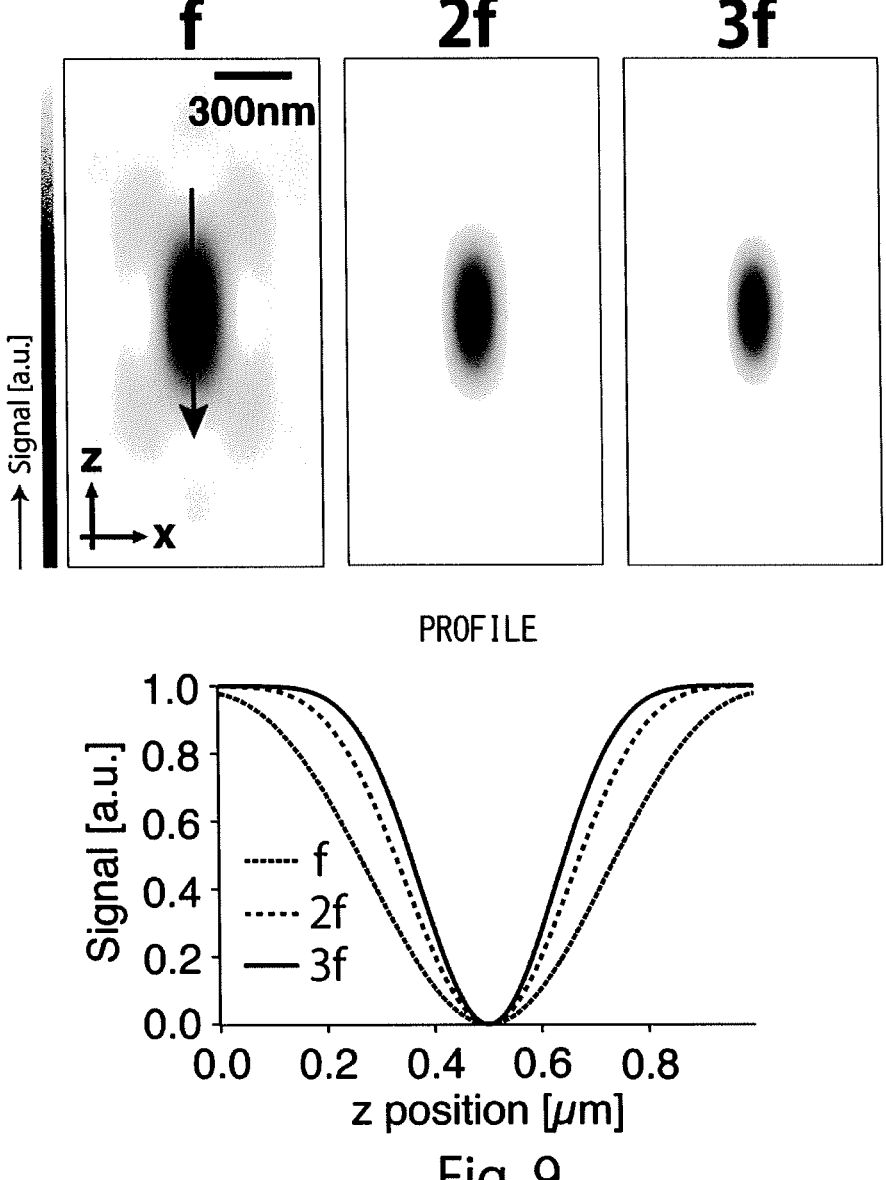
FIG. 9 includes diagrams showing images of minute points composed of the modulation frequency component of the transmitted light signal and its harmonic components as well as profiles of the images in a z-direction.

FIG. 8 and FIG. 9 are diagrams showing simulation results of transmission images of minute points on an XZ-plane. On the upper side in FIG. 8 and FIG. 9, transmission images of minute points composed of the modulation frequency component (f) of the transmission signal, the modulation harmonic component (2f) twice as high as the modulation frequency f, and the modulation harmonic component (3f) three times as high as the modulation frequency f are shown. Lower graphs in FIG. 8 show intensity profiles of the above-described respective images in the X-direction, and lower graphs in FIG. 9 show intensity profiles in the Z-direction. The laser light L1 is linearly polarized light in the y direction as excitation light having a wavelength of 532 nm. The dye is Eosin Y, and the modulation frequency f=10 kHz. The numeric aperture of the objective lens is 1.4.

In FIG. 8 and FIG. 9, the signal intensity profiles of images of minute points respectively composed of signals with the modulation frequency f and the modulation harmonics 2f, 3f of the modulation frequency are shown. A FWHM (full width at half maximum) of the X-direction profile in the image composed of the signal with the modulation frequency f is 174 nm, and a FWHM in the Z-direction profile is 497 nm. A FWHM of the X-direction profile in the image composed of the signal with the modulation harmonics 2f twice as high as the modulation frequency f is 130 nm, and a FWHM in the Z-direction profile is 346 nm. A FWHM of the X-direction profile in the image composed of the signal with the modulation harmonics 3f three times as high as the modulation frequency f is 109 nm, and a FWHM in the Z-direction profile is 288 nm. Consequently, demodulation of a detection signal with a harmonic component n times (n is an integer of 2 or more) as high as the modulation frequency f reduces the extent of an image, which enables imaging with a high spatial resolution.

For example, detection of the second-order modulation harmonic component enables detection on the XY-plane with a spatial resolution 1.34 times higher than in a case of detecting the first-order modulation frequency component. The detection of the second-order and third-order modulation harmonic components in this manner enables the spatial resolution to be improved by 1.34 times and 1.60 times, respectively. This enables imaging with a spatial resolution beyond a diffraction limit, and imaging can be performed with a spatial resolution higher than in the laser microscope of the related art. Further, the light detector 31 detects the transmitted light having the laser light wavelength as the signal light L2, rather than fluorescence. In other words, the transmitted light transmitted through the sample 40 is detected by the light detector 31, which enables detection at high S/N. Thus, imaging with a simple configuration and a high spatial resolution can be achieved. This can contribute to improvement of diagnostic accuracy.

The light detector 31 detects, as the signal light L2, transmitted light having the same wavelength as that of the laser light L1 which is illumination light. Thus, light having the same wavelength as that of laser light should only be detected even in a case of observing higher-order nonlinear effects. That is, the detection of the transmitted light transmitted through the sample 40 enables observation based on the nonlinear effects. That is, since a nonlinear optical loss is measured, a higher-order nonlinear response can be checked easily without preparing an optical component or measurement instrument for shorter wavelengths. This can achieve a higher spatial resolution while using an optical system for a visible range. By separately detecting the nonlinear response, the shape of the sample can be observed three-dimensionally with a spatial resolution beyond the diffraction limit.

The use of the optical microscope according to the present embodiment enables imaging of a high-resolution diagnostic image without using an electron microscope. Thus, the diagnostic accuracy can be improved with an optical microscope which is more inexpensive than an electron microscope. Further, a diagnosis can be performed easily without the need to create a sample for an electron microscope. A high three-dimensional spatial resolution can be obtained, so that a cross-sectional image can be imaged without processing the thick sample 40 into thin sections.

Further, Patent Literature 1 requires a configuration of generating optical harmonics by a higher-order nonlinear optical effect, while in the present embodiment, the use of saturation of absorption in the dye eliminates the need to generate optical harmonics by a higher-order nonlinear optical effect.

Although the laser light intensity is changed using the modulator in the above description, the laser light intensity may be changed by any other methods. For example, as shown in Patent Literature 2, the laser light intensity can be changed stepwise by inserting/removing an ND filter in/from a light path of the laser light L1. Saturation of absorption in the dye is caused to occur when the laser light intensity is maximized. Alternatively, two or more laser light sources different in output intensity may be used to change the laser light intensity. This enables similar effects to be obtained. For example, the laser light intensity is changed such that the laser light is radiated to the sample at least at two intensities of a first intensity at which the signal light has a nonlinear region and a second intensity different from the first intensity. The signal light may have the linear region at the second intensity. The nonlinear increase component of the signal light is calculated based on the intensity of the signal light at the first intensity and the intensity of the signal light at the second intensity. Similar effects can also be obtained in this manner.

Another method is a method for performing demodulation with a plurality of frequencies. For example, a plurality of demodulation frequencies 0(DC), f, 2f, . . . are used. By performing a linear operation of each of demodulation results, a nonlinear signal is extracted. The use of the plurality of demodulation frequencies increases the signal light as compared with demodulation with a single frequency. For example, for extraction of the second-order nonlinear component, demodulation is performed with three demodulation frequencies of 0(DC), f, and 2f. For extraction of the third-order nonlinear component, demodulation is performed with four demodulation frequencies of 0(DC), f, 2f, and 3f. A signal with a frequency of nf or lower should only be measured for an n-order nonlinear signal. For example, an image can be generated by the processing unit 33 performing the above-described processing.

Although only the transmission signal from the sample 40 is detected in the above description, fluorescence from the sample 40 may be detected at the same time. For example, by inserting a dichroic mirror in the light path of the laser light L1, a fluorescent signal generated from the sample 40 can be branched from the laser light L1. A photomultiplier tube (PMT) or a photodiode (PD), for example, may be used for detection of the fluorescent signal. This enables a fluorescent image and an image based on the nonlinear increase component of the transmitted light to be imaged at the same time, which can contribute to a highly accurate pathological diagnosis.

The use of a CW laser light source as the laser light source 11 can achieve a simplified apparatus configuration, and can achieve easy handling. The laser light L1 radiated to the sample 40 may be pulse laser light. For example, the laser light source 11 may be a pulse laser light source. Alternatively, the laser light L1 may be modulated by the modulator 12 to become pulse laser light using the laser light source 11 as a CW laser light source. The use of pulse laser light enables saturation of absorption to occur even if an incident intensity is reduced. This can prevent discoloration of the sample 40.

EXAMPLES

Figure 10:
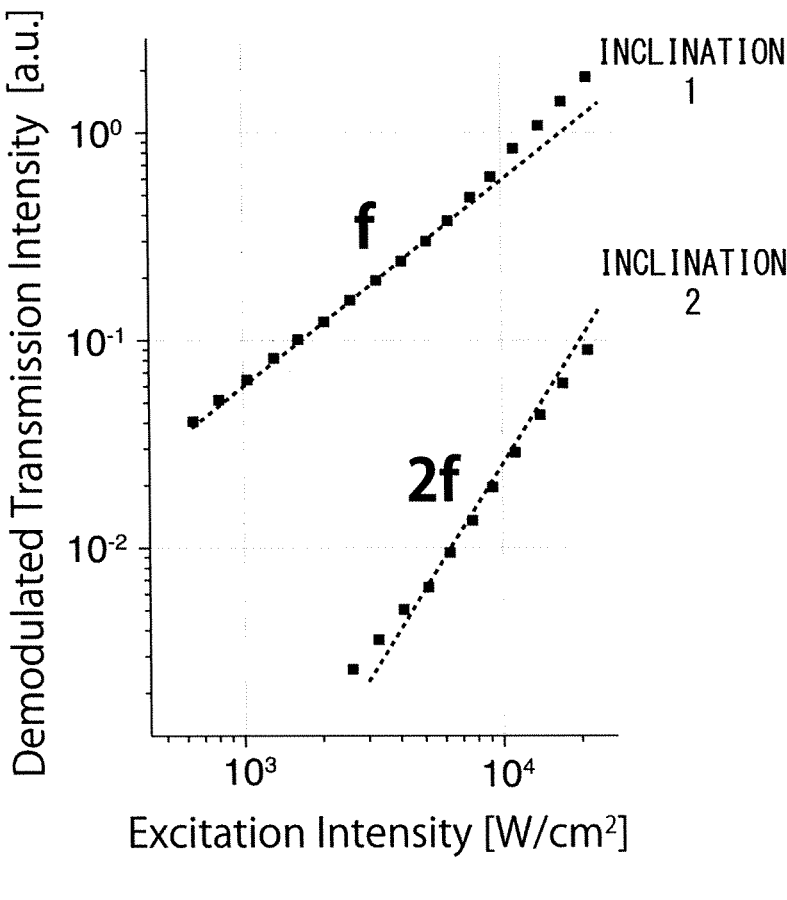
FIG. 10 is a graph of a measurement result showing relations of excitation light intensity to a modulation frequency component of intensity of transmitted light from a dye solution and its harmonic component.

FIG. 10 is a diagram showing a change in intensity of transmitted signal light from a dye solution in a case where the excitation light intensity (laser light intensity) is changed, measured with the optical microscope according to the present embodiment. The horizontal axis represents excitation light intensity, and the vertical axis represents signal intensity. The signal light intensities in FIG. 10 respectively show intensities of transmission signals demodulated with the modulation frequency component (f) and the modulation harmonic component (2f) twice as high as the modulation frequency f.

The dye is Eosin Y, and its solution concentration is 4 mM. The excitation light wavelength is 532 nm, and the numeric aperture of the objective lens is 0.3. The modulation frequency f=10 kHz.

The relation between the transmission signal demodulated with the modulation frequency component (f) and the excitation intensity matches the inclination of 1. That is, the transmission signal demodulated with the modulation frequency component (f) is a linear signal. On the other hand, the transmission signal demodulated with the modulation harmonics (2f) twice as high as the modulation frequency f shows a second-order nonlinear increase with respect to the excitation intensity. That is, by demodulating the transmission signal with the modulation harmonics (2f) twice as high as the modulation frequency f, a second-order nonlinear signal component in the transmission signal can be detected.

Figure 11:
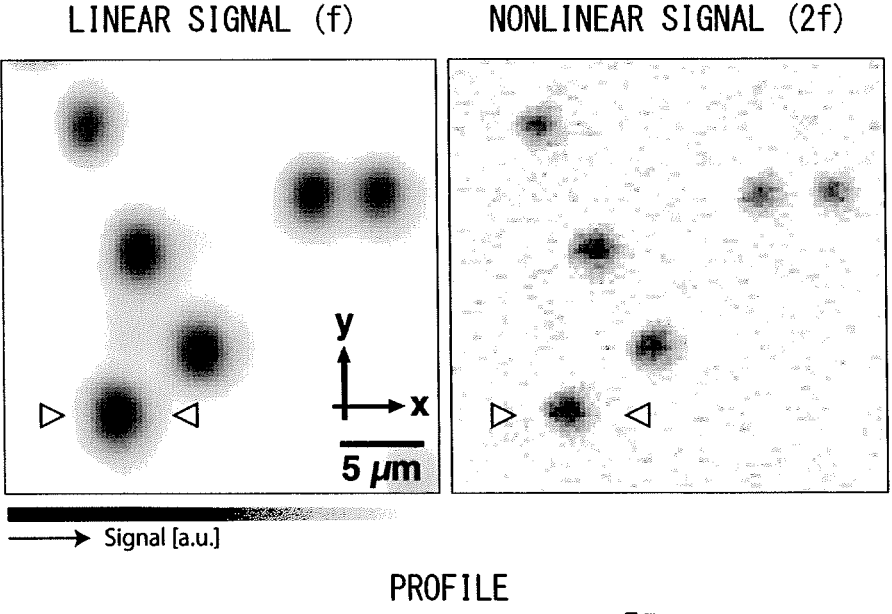
FIG. 11 includes diagrams showing sample images and their profiles.
Figure 11:
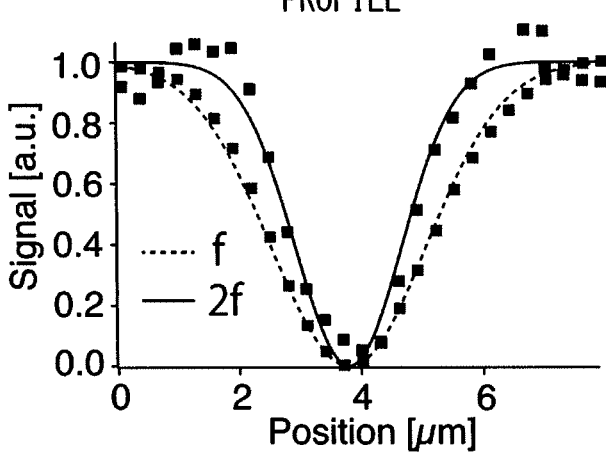

FIG. 11 includes diagrams showing images imaged with the optical microscope according to the present embodiment, and profiles of the images. FIG. 11 shows XY images obtained when 2-μm-diameter polystyrene beads stained with an Eosin Y solution were observed as the sample 40. Specifically, FIG. 11 shows a sample image composed of a signal demodulated with the modulation frequency f and a sample image composed of a signal demodulated with the modulation harmonics 2f twice as high as the modulation frequency f. Further, a lower graph in FIG. 11 shows profiles at marked portions in the respective images.

The laser light wavelength is 532 nm. The exposure time per pixel is 500 μsec. The pixel size is 303 nm/pixel. The numeric aperture of the objective lens is 0.3. The laser light intensity in the image with the modulation frequency f is 56

W/cm², and the laser light intensity in the image with the modulation harmonics 2f is 27 kW/cm².

The image composed of the signal with the modulation harmonics 2f has a spatial resolution higher than that of the image composed of the signal with the modulation frequency f. The size (FWHM) of the bead image composed of the signal with the modulation harmonics 2f is 2.1 μm, and the size (FWHM) of the same bead image composed of the modulation frequency f is 3.0 μm. Detection of the component of the modulation harmonics 2f enables imaging with a high resolution.

Figure 12:
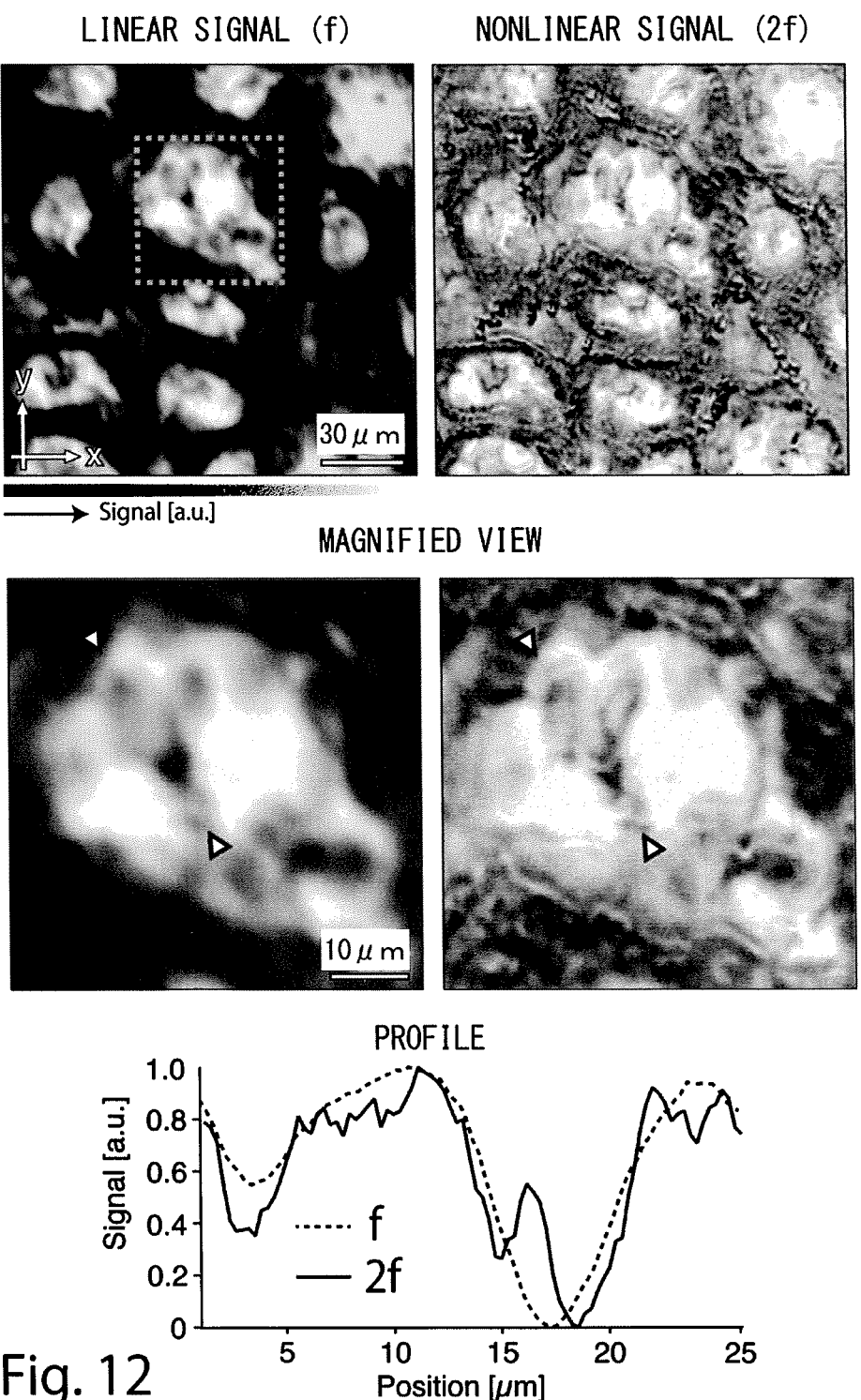
FIG. 12 includes diagrams showing sample images and their profiles.

FIG. 12 shows XY images imaged using rat kidney tissues as a sample. A dye that stained the sample is Eosin Y. Specifically, FIG. 12 shows a sample image composed of a signal demodulated with the modulation frequency f and a sample image composed of a signal demodulated with the modulation harmonics 2f. Further, a lower graph in FIG. 12 shows profiles at marked portions in the respective images.

The laser light wavelength is 532 nm. The exposure time per pixel is 500 μsec. The pixel size is 293 nm/pixel. The numeric aperture of the objective lens is 0.3. The laser light intensity in the image composed of the signal with the modulation frequency f is 100 W/cm², and the laser light intensity in the image composed of the signal with the modulation harmonics 2f is 27 kW/cm².

Figure 13:
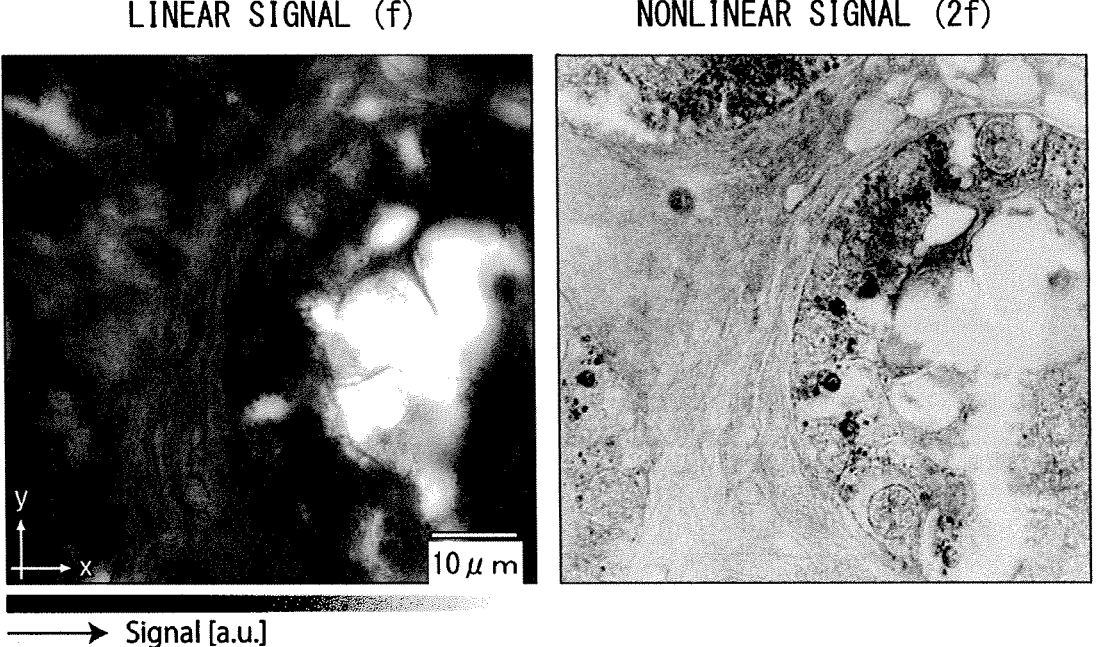
FIG. 13 includes diagrams showing sample images.

FIG. 13 shows XY images of rat kidney tissues imaged using an objective lens having a high numeric aperture NA=1.4. A dye that stained the sample is Eosin Y. Specifically, FIG. 13 shows a sample image composed of a signal demodulated with the modulation frequency f and a sample image composed of a signal demodulated with the modulation harmonics 2f.

The laser light wavelength is 532 nm. The exposure time per pixel is 500 μsec. The pixel size is 59 nm/pixel. The numeric aperture of the objective lens is 1.4. The laser light intensity in the image composed of the signal with the modulation frequency f is 110 W/cm², and the laser light intensity in the image composed of the signal with the modulation harmonics 2f is 130 kW/cm².

Figure 14:
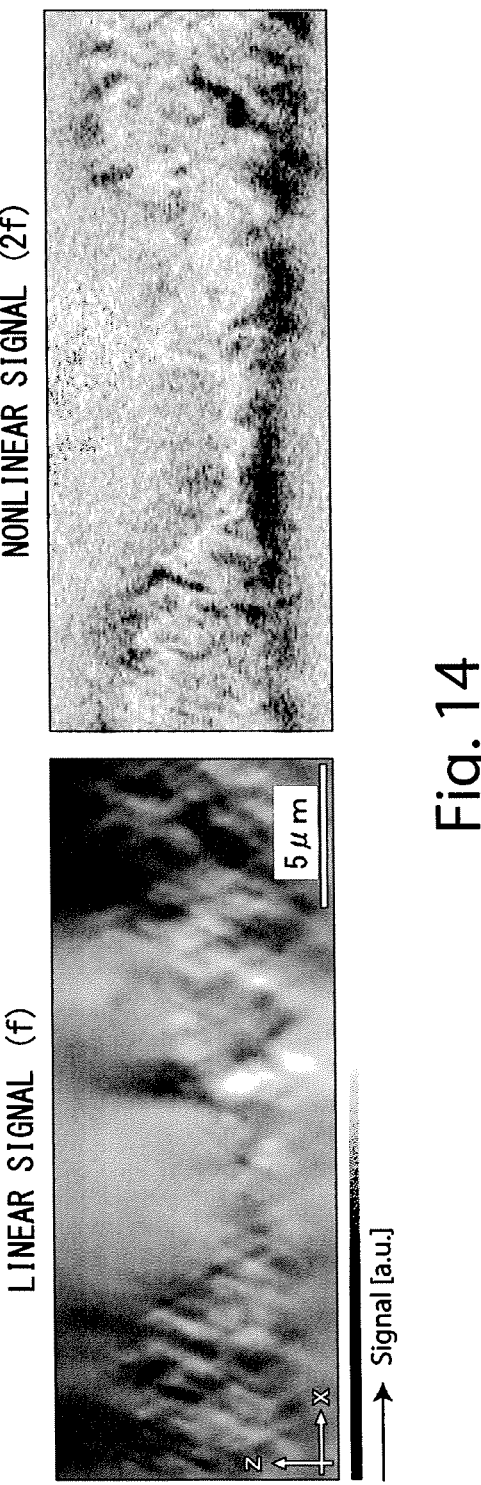
FIG. 14 includes diagrams showing sample images.

FIG. 14 shows XZ images imaged using rat kidney tissues as a sample. A dye that stained the sample is Eosin Y. Specifically, FIG. 14 shows a sample image composed of a signal demodulated with the modulation frequency f and a sample image composed of a signal demodulated with the modulation harmonics 2f twice as high as the modulation frequency f.

The laser light wavelength is 532 nm. The exposure time per pixel is 500 μsec. The pixel size is 98 nm/pixel. The numeric aperture of the objective lens is 1.4. The laser light intensity in the image composed of the signal with the modulation frequency f is 7.9 kW/cm², and the laser light intensity in the image composed of the signal with the modulation harmonics 2f is 390 kW/cm².

Figure 15:
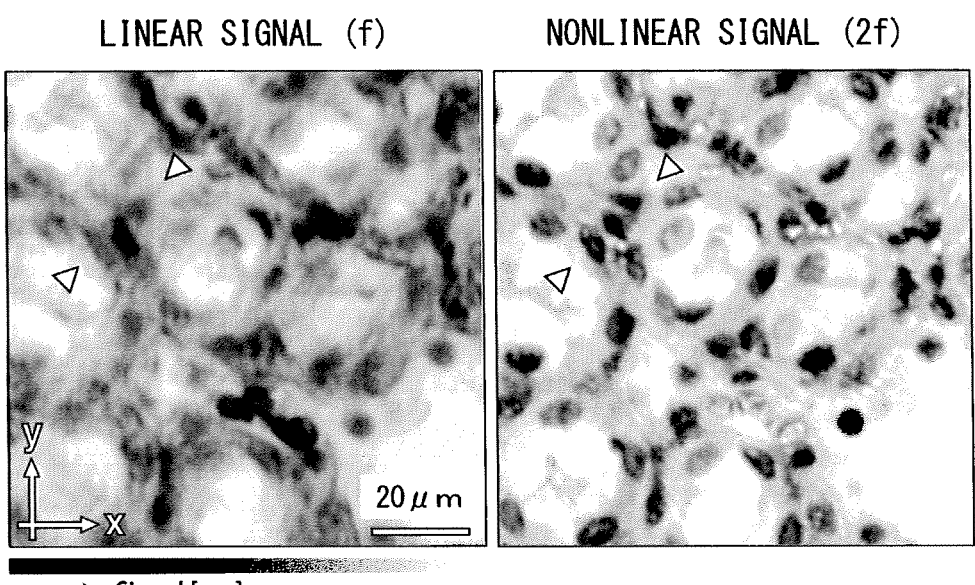
FIG. 15 includes diagrams showing sample images and their profiles.
Figure 15:
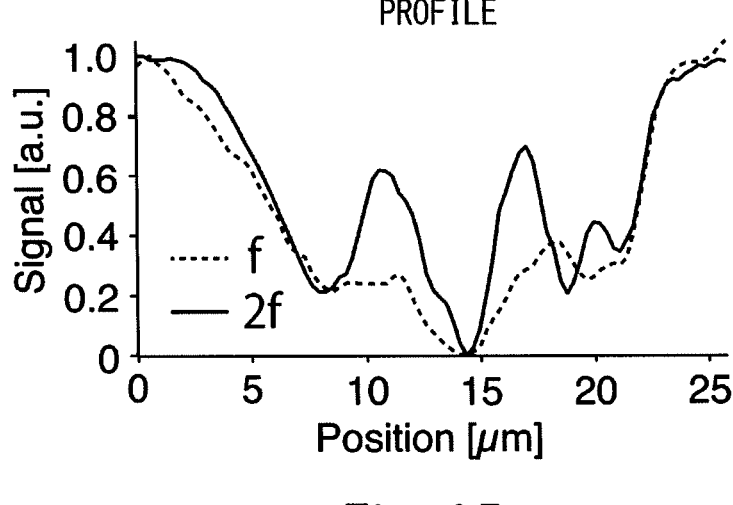

FIG. 15 shows XY images using rat kidney tissues as a sample. A dye that stained the sample is hematoxylin. Specifically, FIG. 15 shows a sample image composed of a signal demodulated with the modulation frequency f and a sample image composed of a signal demodulated with the modulation harmonics 2f. Further, a lower graph in FIG. 15 shows profiles at marked portions in the respective images.

The laser light wavelength is 532 nm. The exposure time per pixel is 500 μsec. The pixel size is 293 nm/pixel. The numeric aperture of the objective lens is 0.3. The laser light intensity in the image composed of the signal with the modulation frequency f is 100 W/cm², and the laser light intensity in the image composed of the signal with the modulation harmonics 2f is 48 kW/cm².

As is apparent from the images in the above-described examples, a high-resolution diagnostic image can be acquired by generating a diagnostic image based on harmonic components included in transmission signals.

Hereinafter, the concentration of a dye that stains the sample 40 and the thickness of the sample 40 will be described. In a case where the amount of the dye in the sample is too large, the amount of light of transmitted light detected by absorption in the dye decreases. Thus, the amount of a nonlinear signal component in the detected transmitted light decreases. For example, in a case where the dye in the sample has a sufficiently high concentration, the amount of the nonlinear signal component in the detected transmitted light decreases. Alternatively, in a case where the sample has a sufficiently large thickness, the amount of the nonlinear signal component in the detected transmitted light decreases. Consequently, it is preferable to set the dye concentration in the sample and the thickness of the sample at certain values or smaller.

Hereinafter, a relation of the transmission signal intensity to the concentration of the dye that stains the sample 40 and the thickness of the sample 40 will be described. The concentration of the dye is denoted by C, and the thickness of the sample 40 in the Z-direction is denoted by L. Note that the thickness L here may be the thickness of a site where light absorption occurs relatively strongly in the sample 40, rather than the thickness of a tissue section or a cell. A product of the concentration C and the thickness L is denoted by a product CL. When denoting the transmission signal intensity by $I_{tr}$, a relation between $I_{tr}$ and the product CL is expressed using Expression (1) and Expression (2). Here, $I_{ex}$ in Expression (1) represents an excitation intensity, and $Wo(x)$ represents a Lambert W function. $I_s$ is called a saturation intensity, content of which will be described later. In Expression (2), $\sigma$ represents an absorption cross-sectional area of the dye, and $N_A$ represents an Avogadro constant.

[Expression 1]

$$I_{tr} = I_S W_0(g(I_{ex})) \qquad (1)$$

[Expression 2]

$$g(I_{ex}) = \frac{I_{ex}}{I_S} \exp\left(\frac{I_{ex}}{I_S}\right) \exp(-N_A \sigma CL) \qquad (2)$$

Here, Is in Expression (1) and Expression (2) is called the saturation intensity, and expressed as shown in Expression (3). In Expression (3), h represents a Planck constant, c represents a light speed, $\lambda$ represents a wavelength of the laser light L1, $k_f$ represents a rate constant in a relaxation process accompanied by radiation from a molecular excited state to a ground state, and $k_{nf}$ represents a rate constant in a relaxation process not accompanied by radiation, respectively.

[Expression 3]

$$I_S = \frac{hc}{2\sigma\lambda}(k_f + k_{nf}) \qquad (3)$$

Figure 16:
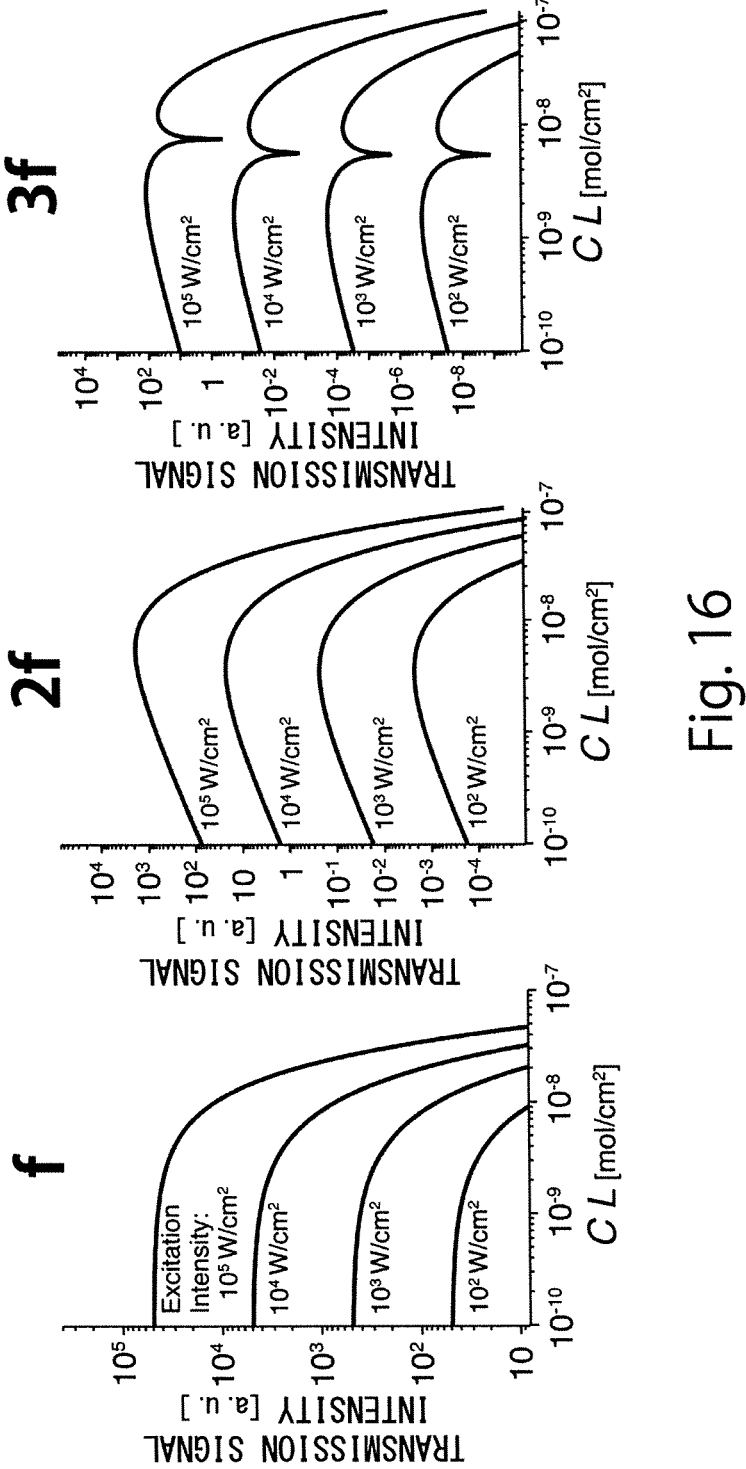
FIG. 16 includes graphs showing relations of a product CL of a concentration C of a dye and a thickness L of a sample to the modulation frequency component of transmitted light intensity and its harmonic components.

FIG. 16 shows relations between the product CL calculated using Expression (1) and Expression (2) and the signal light intensity based on the optical physical property values of Eosin Y. The horizontal axis represents the product CL, and the vertical axis represents signal light (transmitted light) intensity. The modulation frequency f=10 kHz. FIG. 16 shows graphs of the modulation frequency component (f) of transmitted light, the second-order modulation harmonic component (2f), and the third-order modulation harmonic component (3f). FIG. 16 shows calculation results obtained at four excitation light intensities for the respective components.

For example, in a case where the product CL is $4.0\times10^{-9}$ mol/cm$^2$ or smaller, the modulation harmonic components of transmitted light increase as the product CL increases. In a case where the product CL is larger than $4.0\times10^{-9}$ mol/cm$^2$, the second-order or third-order modulation harmonic component decreases as the product CL increases.

In this manner, particularly in the case of imaging a tissue sample stained with Eosin Y, it is preferable to set the product CL at $4.0\times10^{-9}$ mol/cm$^2$ or smaller. A high-resolution diagnostic image can be generated based on a nonlinear increase component of signal light in accordance with saturation of absorption in the dye.

Also in the case of imaging a tissue sample stained with a dye other than Eosin Y, it is preferable to adjust the value of the product CL within a range in which the inclinations of modulation harmonic components of the modulation frequency f of the transmission signal intensity are positive with respect to the product CL. In a case where the sample is stained with any dye, it is preferable that the value of the product CL should be included in the range in which the inclinations of the modulation harmonic components of the modulation frequency f are positive with respect to the product CL. A high-resolution diagnostic image can be generated based on a nonlinear increase component of signal light in accordance with saturation of absorption in the dye.

Note that the laser light wavelength may or may not match an absorption peak wavelength of the dye. In addition, the laser light wavelength may be shifted from the absorption peak wavelength to a shorter wavelength side. This enables imaging with a higher resolution. For example, it is also possible to use ultraviolet laser light as excitation light.

Figure 17:
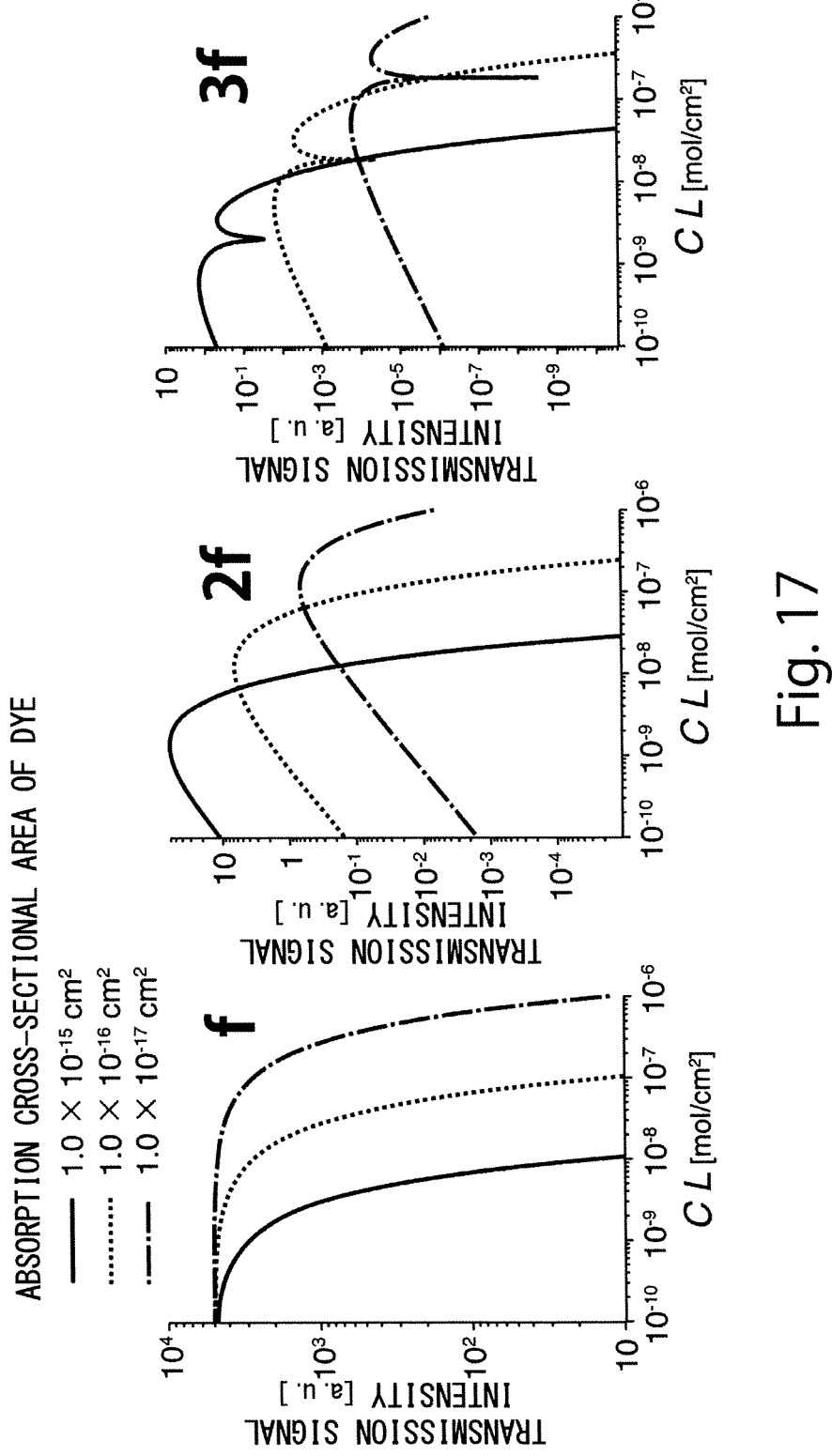
FIG. 17 includes graphs showing relations of the product CL to the modulation frequency component of transmitted light intensity and its harmonic components in a case where an absorption cross-sectional area is changed.

Further, shifting the laser wavelength from the absorption peak wavelength of the dye decreases the absorption cross-sectional area. The range in which modulation harmonic components of the modulation frequency f have positive inclinations with respect to the product CL will change in accordance with the absorption cross-sectional area of the dye. That is, an upper limit value of the range in which the inclinations of the modulation harmonic components of the modulation frequency f of the transmission signal intensity are positive with respect to the product CL will change in accordance with the laser wavelength. This point will be described using FIG. 17. FIG. 17 shows relations between the product CL in a case where the absorption cross-sectional area of the dye is changed and the signal light intensity.

As shown in FIG. 17, in a case where the absorption cross-sectional area is larger, absorption in the dye is more likely to be saturated, so that the upper limit value of the product CL in the range in which the inclinations of the modulation harmonic components 2f, 3f of the modulation frequency f of the transmission signal intensity are positive with respect to the product CL decreases. Thus, as the absorption cross-sectional area is larger, the range in which the inclinations are positive becomes narrower. In addition, the absorption cross-sectional area of the dye changes in accordance with the laser wavelength. By changing the laser wavelength, the value of the product CL can be included in the range in which the inclinations of the modulation harmonic components of the modulation frequency f of the transmission signal intensity are positive with respect to the product CL. That is, by selecting a laser wavelength having an absorption cross-sectional area appropriate for the dye, a high-resolution image can be imaged.

Note that the sample 40 may be stained with a dye other than Eosin and hematoxylin. Alternatively, the sample 40 may be stained with two or more dyes. For example, a staining method such as immunostaining, PAS (periodic acid-Schiff) stain, Masson trichrome stain, Congo red stain, Oil red O stain, Azan stain, Giemsa stain, or Sudan III stain may be used. As a matter of course, the type of the dye that stains the sample 40, the staining method, and the like are not limited to the above-described examples.

Although the invention made by the inventors of the present invention has been specifically described above based on the embodiment, it goes without saying that the present invention is not limited to the above-described embodiment, and can be variously modified within the scope not departing from the spirit of the invention.

This application is based upon and claims the benefit of priority from Japanese Patent Application No. 2021-14272 filed on Feb. 1, 2021, the disclosure of which is incorporated herein in its entirety by reference.

REFERENCE SIGNS LIST

1 OPTICAL MICROSCOPE
11 LASER LIGHT SOURCE
12 MODULATOR
13 GALVANO-MIRROR
14 OBJECTIVE LENS
21 CONDENSER LENS
31 LIGHT DETECTOR
32 LOCK-IN AMPLIFIER
33 PROCESSING UNIT
34 BEAM SAMPLER
35 REFERENCE LIGHT DETECTOR
40 SAMPLE

The invention claimed is:

1. An optical microscope for imaging an image for tissue observation or pathological diagnosis, comprising:
    at least one laser light source configured to generate laser light with a laser wavelength for illuminating a sample containing a light absorbing material;
    a lens configured to focus the laser light to be focused on the sample;
    scanning means for changing a focusing position of the laser light on the sample; and
    a light detector configured to detect laser light transmitted through the sample as signal light with the laser wavelength, wherein
    a laser light intensity is changed to obtain a nonlinear region in which the laser light intensity and a signal light intensity have a nonlinear relation due to occurrence of saturation of absorption in the light absorbing material when the laser light intensity is maximized, and
    an image is generated based on a nonlinear component of the signal light based on the saturation of absorption in the light absorbing material,
    wherein
    the light absorbing material is a dye,
    the sample contains a tissue, a cell, or a bacterium stained with the dye,
    the laser wavelength is selected so that a value of a product CL is included in a range in which an inclination of a modulation harmonic component of a modulation frequency f included in a transmission signal is positive with respect to the product CL,
    the laser light is intensity modulated with the modulation frequency f,
    C indicates a concentration of the dye, and
    L indicates a thickness of the sample.

2. The optical microscope according to claim 1, wherein the dye that stains the sample is Eosin Y, and
    a product CL of a concentration C of the dye and a thickness L of the sample is 4.0×10-9 mol/cm2 or smaller.

3. The optical microscope according to claim 1, wherein the focusing position of the laser light is changed in a thickness direction of the sample.

4. The optical microscope according to claim 1, wherein the laser light source generates CW (continuous wave) laser light.

5. The optical microscope according to claim 1, wherein the laser light incident on the sample is pulse laser light.

6. An imaging method for imaging an image for tissue observation or pathological diagnosis using an optical microscope, the imaging method comprising the steps of:
    generating laser light with a laser wavelength for illuminating a sample containing a light absorbing material;
    focusing the laser light to be focused on the sample;
    changing a focusing position of the laser light on the sample;
    detecting laser light with the laser wavelength transmitted through the sample as signal light;
    changing a laser light intensity to obtain a nonlinear region in which the laser light intensity and a signal light intensity have a nonlinear relation due to occurrence of saturation of absorption in the light absorbing material when the laser light intensity is maximized; and
    generating an image based on a nonlinear component of the signal light based on the saturation of absorption in the light absorbing material,
    wherein
    the light absorbing material is a dye, and
    the sample contains a tissue, a cell, or a bacterium stained with the dye,
    the laser wavelength is selected so that a value of a product CL is included in a range in which an inclination of a modulation harmonic component of a modulation frequency f included in a transmission signal is positive with respect to the product CL,
    the laser light is intensity modulated with the modulation frequency f,
    C indicates a concentration of the dye, and
    L indicates a thickness of the sample.

7. The imaging method according to claim 6, wherein the dye is Eosin Y, and
    a product CL of a concentration C of the dye and a thickness L of the sample is 4.0×10-9 mol/cm2 or smaller.

8. The imaging method according to claim 6, wherein the focusing position of the laser light is changed in a thickness direction of the sample.

9. The imaging method according to claim 6, wherein the laser light is CW (continuous wave) laser light.

10. The imaging method according to claim 6, wherein the laser light incident on the sample is pulse laser light.

* * * * *